United States Patent [19]
Kaddurah-Daouk

[11] Patent Number: 5,998,457
[45] Date of Patent: Dec. 7, 1999

[54] CREATINE ANALOGUES FOR TREATMENT OF OBESITY

[75] Inventor: Rima Kaddurah-Daouk, Belmont, Mass.

[73] Assignee: Avicena Group, Inc., Cambridge, Mass.

[21] Appl. No.: 08/736,967

[22] Filed: Oct. 25, 1996

Related U.S. Application Data

[60] Provisional application No. 60/005,882, Oct. 26, 1995.

[51] Int. Cl.$^6$ .................. A61K 31/415; A61K 31/195
[52] U.S. Cl. .................. 514/392; 514/565; 514/825; 514/866; 514/909
[58] Field of Search .................. 514/565, 825, 514/866, 909, 392

[56] References Cited

U.S. PATENT DOCUMENTS

| | | | |
|---|---|---|---|
| 5,091,404 | 2/1992 | Elgebaly | 514/401 |
| 5,321,030 | 6/1994 | Kaddurah-Daouk et al. | 514/275 |
| 5,324,731 | 6/1994 | Kaddurah-Daouk et al. | 514/275 |
| 5,627,172 | 5/1997 | Almada et al. | 514/120 |

FOREIGN PATENT DOCUMENTS

| | | |
|---|---|---|
| WO 90/09192 | 8/1990 | WIPO . |
| WO 92/08456 | 5/1992 | WIPO . |
| WO 94/16687 | 8/1994 | WIPO . |

OTHER PUBLICATIONS

Annesley, T.M. and J.B. Walker (1977) "Cyclocreatine Phosphate as a Substitute for Creatine Phosphate in Vertebrate Tissues. Energetic Considerations" *Biochem. Biophys. Res. Commun.* 74(1): 185–190.

Coleman, D.L. (1978) "Obese and Diabetes: Two Mutant Genes Causing Diabetes–Obesity Syndromes in Mice" *Diabetologia* 14: 141–148.

Cramer, F. et al. (1962) "Die Synthese der Argininphosphorsäure und die Reaktion von Isoureidophosphonaten mit Aminen" *Chemische Berichte Jahrg.* 95: 1670–1682.

Friedman, J.M. and R.L. Leibel (1990) "Tacking a Weighty Problem" *Cell* 69: 217–220.

Friedman, J.L. et al. (1991) "Molecular Mapping of the Mouse *ob* Mutation" *Genomics* 11: 1054–1062.

Griffiths, G.R. and J.B. Walker (1976) "Accumulation of Analog of Phosphocreatine in Muscle of Chicks Fed 1–Carboxymethyl–2–iminoimidazlidine (Cyclocreatine)" *J. Biol. Chem.* 251: 2049–2054.

Halaas, J.L. et al. (1995) "Weight–Reducing Effects of the Plasma Protein Encoded by the *obese* Gene" *Science* 269: 543–546.

Lowe. G. and B.S. Sproat (1980) "Evidence for an Associative Mechanism in the Phosphoryl Transfer Step Catalyzed by Rabbit Muscle Creatine Kinase" *J. Biol. Chem.* 225(9): 3944–3951.

McLaughlin, A.C. and M. Cohn (1972) "Specificity of Creatine Kinase for Guanidino Substrates" *J. Biol. Chem.* 247(13): 4382–4388.

Roberts, J.J. and J.B. Walker (1983) "Synthesis and Accumulation of an Extremely Stable High–Energy Phosphate Compound by Muscle, Heart, and Brain of Animals. . . " *Arch. Biochem. Biophys.* 220: 563–571.

Roberts, J.J. and J.B. Walker (1995) "Higher Homolog and *N* –Ethyl Analog of Creatine as Synthetic Phosphagen Precursors in Brain, Heart, and Muscle, Repressors of Liver Amidinotransferase, and Substrates for Creatine Catabolic Enzymes" *J. Biol. Chem.* 260: 13502–13508.

Rowley, G.L. et al. (1971) "On the Specificity of Creatine Kinase. New Glycocyamines and Glycocyamine Analogs Related to Creatine" *J. Am. Chem. Soc.* 93(21): 5542–5551.

Walliman, T. et al. (1992) "Intracellular compartmentation, stucture and function of creatine kinase isoenzymes in tissues with high and fluctating energy demands: the 'phosphocreatine circuit' for cellular energy" *Biochem. J.* 281: 21–40.

Zhang, Y. et al. (1994) "Positional cloning of the mouse *obese* gene and its human homologue" *Nature* 372: 425–432.

*Primary Examiner*—Kimberly Jordan
*Attorney, Agent, or Firm*—Lahive & Cockfield, LLP

[57] ABSTRACT

The present invention relates to the use of creatine compounds for treating or preventing a metabolic disorder related to body weight control such as obesity, and it's associated diseases in a patient experiencing said disorder. The creatine compounds which can be used in the present method include (1) analogues of creatine which can act as substrates or substrate analogues for the enzyme creatine kinase; (2) compounds which can act as inhibitors of creatine kinase; (3) compounds which can modulate the creatine transporter (4) N-phosphocreatine analogues bearing transferable or non-transferable moieties which mimic the N-phosphoryl group. (5) compounds which modify the association of creatine kinase with other cellular components.

20 Claims, No Drawings

CREATINE ANALOGUES FOR TREATMENT OF OBESITY

RELATED APPLICATIONS

The present application is a continuation-in-part of and claims priority to Provisional Application U.S. Ser. No. 60/005,882, filed Oct. 26, 1995, the entire disclosure of which is incorporated herein by reference.

FIELD OF INVENTION

The present invention provides for new use for creatine compounds (creatine analogues and compounds which modulate one or more of the structural or functional components of the creatine kinase/creatine phosphate system) as therapeutic agents. More particularly, the present invention provides a method of treating or preventing certain metabolic disorders of human and animal metabolism relating to aberrant body weight regulation as manifested in obesity and it's related disorders.

BACKGROUND OF THE INVENTION

There are several metabolic diseases of human and animal metabolism, eg., obesity and severe weight loss that relate to energy imbalance—where caloric intake versus energy expenditure—is imbalanced. Obesity, which can be defined as a body weight more than 20% in excess of the ideal body weight, is a major health problem in Western affluent societies. It is associated with an increased risk for cardiovascular disease, hypertension, diabetes, hyperlipidaemia and an increased mortality rate. Obesity is the result of a positive energy balance, as a consequence of an increased ratio of caloric intake to energy expenditure. The molecular factors regulating food intake and body weight balance are incompletely understood. Five single-gene mutations resulting in obesity have been described in mice, implicating genetic factors in the etiology of obesity. (Friedman, J. M., and Leibel, R. L. Cell 69: 217–220 (1990)). In the ob mouse a single gene mutation, obese, results in profound obesity, which is accompanied by diabetes (Friedman, J. M., et. al. Genomics 11: 1054–1062 (1991)). Cross-circulation experiments have suggested that the ob mice are deficient of a blood-borne factor regulating nutrient intake and energy metabolism (Coleman, D. L. Diabetologia 14: 141–148 (1978)). Using positional cloning technologies, the mouse ob gene, and subsequently its human homologue, have been recently cloned (Zhang, Y., et. al., Nature 372: 425–432 (1994)). Daily intraperitoneal injections of either mouse or human recombinant OB protein reduced the body weight of obese mice ob/ob by 30% after 2 weeks of injection. The protein reduced food intake and increased energy expenditure in the ob/ob mice (Halaas et. al., Science 269: 543–546 (1995)).

Cachexia on the other hand is characterized by severe weight loss and imbalanced energy expenditure, examples being patients with cancer or HIV infections.

The creatine kinase/creatine phosphate system is an energy generating system operative predominantly in the brain, muscle, heart, retina, adipose tissue and the kidney (Walliman et. al., Biochem. J. 281: 21–40 (1992)). The components of the system include the enzyme creatine kinase (CK), the substrates creatine (Cr), creatine phosphate (CrP), ATP,ADP, and the creatine transporter. The enzyme catalyses reversibly the transfer of a phosphoryl group from CrP to ADP to generate ATP which is the main source of energy in the cell. This system represents the most efficient way to generate energy upon rapid demand. The creatine kinase isoenzymes are found to be localized at sites where rapid rate of ATP replenishment is needed such as around ion channels and ATPase pumps. Some of the functions associated with this system include efficient regeneration of energy in the form of ATP in cells with fluctuating and high energy demand, energy transport to different parts of the cell, phosphoryl transfer activity, ion transport regulation, and involvement in signal transduction pathways.

The substrate Cr is a compound which is naturally occurring and is found in mammalian brain, skeletal muscle, retina, adipose tissue and the heart. It's phosphorylated form CrP is also found in the same organs and is the product of the CK reaction. Both compounds can be easily synthesized and are believed to be non toxic to man. A series of creatine analogues have also been synthesized and used as probes to study the active site of the enzyme. Kaddurah-Daouk et al. (WO 92/08456 published May 29, 1992 and WO 90/09192, published Aug. 23, 1990; U.S. Pat. No. 5,321,030; and U.S. Pat. No. 5,324,731) described methods for inhibiting growth, transformation, or metastasis of mammalian cells using related compounds. Examples of such compounds include cyclocreatine, homocyclocreatine and beta guanidino propionic acid. These same inventors have also demonstrated the efficacy of such compounds for combating viral infections (U.S. Pat. No. 5,321,030). Elgebaly in U.S. Pat. No. 5,091,404 discloses the use of cyclocreatine for restoring functionality in muscle tissue. Cohn in PCT publication No. WO 94/16687 describes a method for inhibiting the growth of several tumors using creatine and related compounds.

It is an object of the present invention to provide methods for treatment of metabolic diseases that relate to deregulated body weight by administering to an afflicted individual an amount of a compound or compounds which modulate one or more of the structural or functional components of the creatine kinase/creatine phosphate system sufficient to prevent, reduce or ameliorate the symptoms of the disease. These compounds are collectively referred to as "creatine compounds."

SUMMARY OF THE INVENTION

The present invention provides a method of treating or preventing a metabolic disorder which relates to an imbalance in the regulation of body weight. Examples would be obesity and its related disorders (such as cardiovascular disease, hypertension, diabetes, hyperlipidaemia, osteoporosis and osteoarthritis) and severe weight loss. It consists of administering to a patient susceptible to or experiencing said disorder a creatine compound (creatine analogues and compounds which modulate one or more of the structural or functional components of the creatine kinase/creatine phosphate system) as therapeutic in the form of a pharmacologically acceptable salt as the pharmaceutical agent effective to treat or prevent the disease or condition.

Obesity is the result of a positive energy balance, as a consequence of an increased ratio of caloric intake to energy expenditure while severe weight loss is a result of a negative energy balance. The creatine kinase system is known to be involved in energy metabolism and it's substrates creatine phosphate, and ATP are among the highest energy compounds in the cell. It is now possible to modify this system and come up with compounds that can change energy balance and subsequently treat, prevent or ameliorate the diseases mentioned. One can increase energy state or decrease it by using substrates or inhibitors for the enzyme creatine kinase, or modulators of the enzyme system (compounds which modify any of its components) such as the creatine transporter.

The present invention also provides compositions containing creatine compounds in combination with a pharmaceutically acceptable carrier. Also, they could be used in combination with effective amounts of standard chemotherapeutic agents which act on regulating body weight and others to prophylactically and/or therapeutically treat a subject with a disease related to body weight control.

Packaged drugs for treating subjects having energy imbalance resulting in weight loss or gain are also the subject of the present invention. The packaged drugs include a container holding the creatine compound, in combination with a pharmaceutically acceptable carrier, along with instructions for administering the same for the purpose of preventing, ameliorating, arresting or eliminating a disease related to glucose level regulation.

By treatment is meant the amelioration or total avoidance of the metabolic disorder as described herein. By prevention is meant the avoidance of a currently recognized disease state, as described herein, in a patient evidencing some or all of the metabolic disorders described above.

For all of these purposes, any convenient route of systemic administration is employed, e.g., orally, parenterally, intranasally or intrarectally. The above compositions may be administered in a sustained release formulation. By sustained release is meant a formulation in which the drug becomes biologically available to the patient at a measured rate over a prolonged period. Such compositions are well known in the art.

DETAILED DESCRIPTION OF THE INVENTION

The method of the present invention generally comprises administering to an individual afflicted with a disease or susceptible to a disease involving body weight regulation, an amount of a compound or compounds which modulate one or more of the structural or functional components of the creatine kinase/phosphocreatine system sufficient to prevent, reduce or ameliorate symptoms of the disease. Components of the system which can be modulated include the enzyme creatine kinase, the substrates creatine, creatine phosphate, ADP, ATP, and the transporter of creatine. As used herein, the term "modulate" means to change, affect or interfere with the functioning of the components in the creatine kinase/creatine phosphate enzyme system.

The creatine kinase/creatine phosphate system is an energy generating system operative predominantly in the brain, muscle, heart, retina, adipose tissue and the kidney (Walliman et. al., Biochem. J. 281: 21–40 (1992)). The components of the system include the enzyme creatine kinase (CK), the substrates creatine (Cr), creatine phosphate (CrP), ATP,ADP, and the creatine trasporter. The enzyme catalyses reversibly the transfer of a phosphoryl group from CrP to ADP to generate ATP which is the main source of energy in the cell. This system represents the most efficient way to generate energy upon rapid demand. The creatine kinase isoenzymes are found to be localized at sites where rapid rate of ATP replenishment is needed such as around ion channels and ATPase pumps. Some of the functions associated with this system include efficient regeneration of energy in the form of ATP in cells with fluctuating and high energy demand, energy transport to different parts of the cell, phosphoryl transfer activity, ion transport regulation, and involvement in signal transduction pathways.

Brown and white adipose tissue both contain creatine kinase and the substrates creatine and creatine phosphate, with activity of the enzyme 50 times higher in brown tissue (Bertlet et al., Biochim Biophys. Acta 437:166–174 (1976)). Brown fat tissue is responsible for energy expenditure and heat generation through the process of non-shivering thermogenesis. It was suggested that creatine may be involved in co-promoting mitochondrial respiration for thermogenesis.

The substrate Cr is a compound which is naturally occurring and is found in mammalian brain, skeletal muscle, retina and the heart. It's phosphorylated form CrP is also found in the same organs and is the product of the CK reaction. Both compounds can be easily synthesized and are believed to be non toxic to man. A series of creatine analogues have also been synthesized and used as probes to study the active site of the enzyme. Kaddurah-Daouk et al. (WO 92/08456 published May 29, 1992 and WO 90/09192, published Aug. 23, 1990; U.S. Pat. No. 5,321,030; and U.S. Pat. No. 5,324,731) described methods for inhibiting growth, transformation, or metastasis of mammalian cells using related compounds. Examples of such compounds include cyclocreatine, homocyclocreatine and beta guanidino propionic acid. These same inventors have also demonstrated the efficacy of such compounds for combating viral infections (U.S. Pat. No. 5,321,030). Elgebaly in U.S. Pat. No. 5,091,404 discloses the use of cyclocreatine for restoring functionality in muscle tissue. Cohn in PCT publication No. WO 94/16687 describes a method for inhibiting the growth of several tumors using creatine and related compounds.

The term "creatine compound" will be used herein to include creatine, and compounds which are structurally similar to it and analogues of creatine and creatine phosphate. The term "creatine compound" also includes compounds which "mimic" the activity of creatine, creatine phosphate, or creatine analogues i.e., compounds which modulate the creatine kinase system. The term "mimics" is intended to include compounds which may not be structurally similar to creatine but mimic the therapeutic activity of the creatine analogues or structurally similar compounds. The term creatine compounds will also include inhibitors of creatine kinase, ie. compounds which inhibit the activity of the enzyme creatine kinase, molecules that inhibit the creatine transporter or molecules that inhibit the binding of the enzyme to other structural proteins or enzymes or lipids. The term "modulators" of the creatine kinase system" are compounds which modulate the activity of the enzyme, or the activity of the transporter of creatine, or the ability of the enzyme to associate with other cellular components. These could be substrates for the enzyme and they would have the ability to build in their phosphorylated state intracellularly. These types of molecules are also included in our term creatine compounds. The term creatine "analogue" is intended to include compounds which are structurally similar to creatine, compounds which are art-recognized as being analogues of creatine, and/or compounds which share the same function as creatine.

Creatine (α also known as N-(aminoiminomethyl)-N-methyl glycine; methylglycosamine or N-methyl-guanidino acetic acid is a well-known substance. (see the Merck Index, Eleventh Edition No. 2570, 1989). Creatine is phosphorylated chemically or enzymatically to creatine kinase to generate creatine phosphate, which is also well known (see The Merck Index, No.7315). Both creatine and creatine phosphate (phosphocreatine) can be extracted from animals or tissue or synthesized chemically. Both are commercially available.

Cyclocreatine is an essentially planer cyclic analogue of creatine. Although cyclocreatine is structurally similar to creatine, the two compounds are distinguishable both kinetically and thermodynamically. Cyclocreatine is phosphorylated efficiently by the enzyme creatine kinase in the forward reaction, both in vitro and in vivo. Rowley, G. L., J.AM. Chem.Soc. 93:5542–5551 (1971); McLaughlin, A. C. et. al. J. Biol. Chem. 247, 4382–4388 (1972). It represents a class of substrate analogues of creatine kinase and which are believed to be active.

Examples of substances (creatine analogues) known or believed to modify the creatine kinase/creatine phosphate system are listed in Tables 1 and 2.

TABLE 1

CREATINE ANALOGS

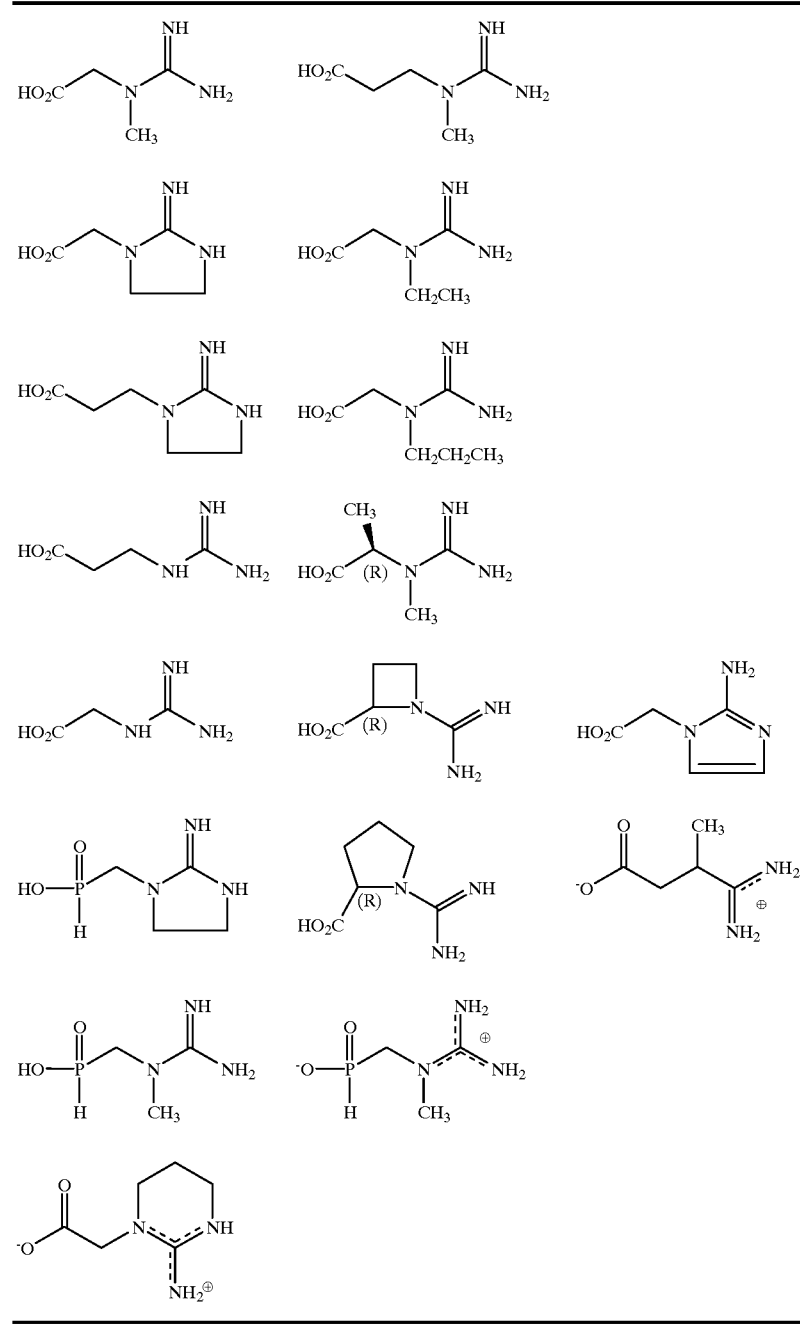

TABLE 2

CREATINE PHOSPHATE ANALOGS

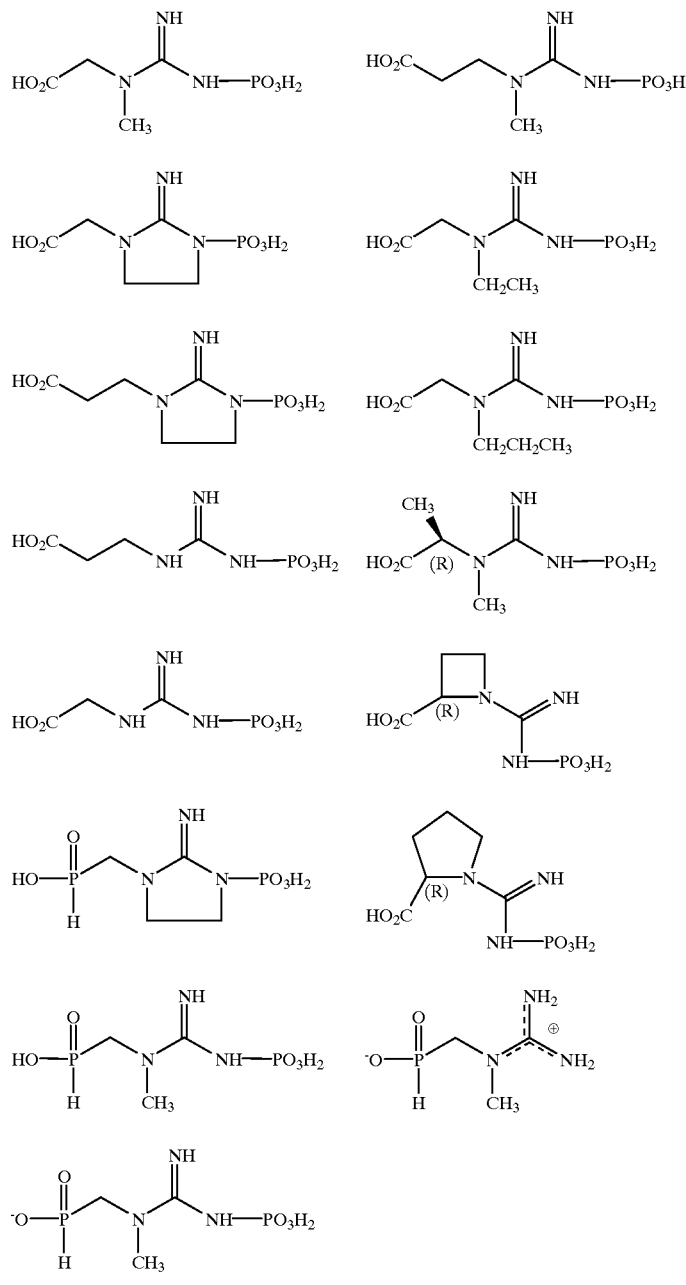

Most of these compounds have been previously synthesized for other purposes (Rowley et. al., J.Am.Chem.Soc., 93: 5542–5551, (1971); Mclaughlin et. al., J.Biol.Chem., 247: 4382–4388 (1972) Nguyen, A. C. K., "Synthesis and enzyme studies using creatine analogues", Thesis, Dept of Pharmaceutical Chemistry, Univ. Calif., San Francisco, 1983; Lowe et al., J. Biol. Chem., 225:3944–3951(1980); Roberts et. al., J. Biol. Chem., 260:13502–13508 (1995) Roberts et. al., Arch. biochem. Biophy., 220:563–571, 1983, and Griffiths et. al., J.Biol. Chem., 251: 2049–2054 (1976). The contents of all of the forementioned references are expressly incorporated by reference. Further to the forementioned references, Kaddurah-Daouk et. al., (WO 92/08456; WO 90/09192; U.S. Pat. No. 5,324,731; U.S. Pat. No. 5,321,030) also provide citations for the synthesis of a plurality of creatine analogues. The contents of all the aforementioned references and patents are incorporated herein by reference.

It will be possible to modify the substances described below to produce analogues which have enhanced characteristics, such as greater specificity for the enzyme, enhanced solubility or stability, enhanced cellular uptake, or better biding activity. Salts of products may be exchanged to other salts using standard protocols.

Bisubstrate analogues of creatine kinase and non hydrolyizable substrate analogues of creatine phosphate (non transferable moieties which mimic the N phosphoryl group of creatine phosphate) can be designed readily and would be examples of creatine kinase modulators. Creatine phosphate compounds can be synthesized chemically or enzymatically. The chemical synthesis is well known. Annesley, T. M., Walker, J. B., Biochem.Biophys.Res. Commun., 74: 185–190 (1977); Cramer, F., Scheiffele, E., VOLLMAR, A., Chem.Ber., 95:1670–1682 (1962).

Creatine compounds which are particularly useful in this invention include those encompassed by the following general formula:

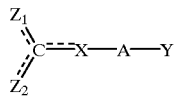

and pharmaceutically acceptable salts thereof, wherein:
 a) Y is selected from the group consisting of: —$CO_2H$—NHOH, —$NO_2$, —$SO_3H$, —C(=O)$NHSO_2$J and —P(=O)(OH)(OJ), wherein J is selected from the group consisting of: hydrogen, $C_1$–$C_6$ straight chain alkyl, $C_3$–$C_6$ branched alkyl, $C_2$–$C_6$ alkenyl, $C_3$–$C_6$ branched alkenyl, and aryl;
 b) A is selected from the group consisting of: C, CH, $C_1$–$C_5$ alkyl, $C_2$–$C_5$ alkenyl, $C_2$–$C_5$ alkynyl, and $C_1$–$C_5$ alkoyl chain, each having 0–2 substituents which are selected independently from the group consisting of:
  1) K, where K is selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: bromo, chloro, epoxy and acetoxy;
  2) an aryl group selected from the group consisting of: a 1–2 ring carbocycle and a 1–2 ring heterocycle, wherein the aryl group contains 0–2 substituents independently selected from the group consisting of: —$CH_2$L and —$COCH_2$L where L is independently selected from the group consisting of: bromo, chloro, epoxy and acetoxy; and
  3) —NH—M, wherein M is selected from the group consisting of: hydrogen, $C_1$–$C_4$ alkyl, $C_2$–$C_4$ alkenyl, $C_1$–$C_4$ alkoyl, $C_3$–$C_4$ branched alkyl, $C_3$–$C_4$ branched alkenyl, and $C_4$ branched alkoyl;
 c) X is selected from the group consisting of $NR_1$, $CHR_1$, $CR_1$, O and S, wherein $R_1$ is selected from the group consisting of:
  1) hydrogen;
  2) K where K is selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: bromo, chloro, epoxy and acetoxy;
  3) an aryl group selected from the group consisting of a 1–2 ring carbocycle and a 1–2 ring heterocycle, wherein the aryl group contains 0–2 substituents independently selected from the group consisting of: —$CH_2$L and —$COCH_2$L where L is independently selected from the group consisting of: bromo, chloro, epoxy and acetoxy;
  4) a $C_5$–$C_9$ a-amino-w-methyl-w-adenosylcarboxylic acid attached via the w-methyl carbon;
  5) 2 $C_5$–$C_9$ a-amino-w-aza-w-methyl-w-adenosylcarboxylic acid attached via the w-methyl carbon; and
  6) a $C_5$–$C_9$ a-amino-w-thia-w-methyl-w-adenosylcarboxylic acid attached via the w-methyl carbon;
 d) $Z_1$ and $Z_2$ are chosen independently from the group consisting of: =O, —$NHR_2$, —$CH_2R_2$, —$NR_2OH$; wherein $Z_1$ and $Z_2$ may not both be =O and wherein $R_2$ is selected from the group consisting of:
  1) hydrogen;
  2) K, where K is selected from the group consisting of: $C_1$–$C_6$ straight alkyl; $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: bromo, chloro, epoxy and acetoxy;
  3) an aryl group selected from the group consisting of a 1–2 ring carbocycle and a 1–2 ring heterocycle, wherein the aryl group contains 0–2 substituents independently selected from the group consisting of: —$CH_2$L and —$COCH_2$L where L is independently selected from the group consisting of: bromo, chloro, epoxy and acetoxy;
  4) 2 $C_4$–$C_8$ a-amino-carboxylic acid attached via the w-carbon;
  5) B, wherein B is selected from the group consisting of: —$CO_2H$—NHOH, —$SO_3H$, —$NO_2$, OP(=O)(OH)(OJ) and —P(=O)(OH)(OJ), wherein J is selected from the group consisting of: hydrogen, $C_1$–$C_6$ straight alkyl, $C_3$–$C_6$ branched alkyl, $C_2$–$C_6$ alkenyl, $C_3$–$C_6$ branched alkenyl, and aryl, wherein B is optionally connected to the nitrogen via a linker selected from the group consisting of: $C_1$–$C_2$ alkyl, $C_2$ alkenyl, and $C_1$–$C_2$ alkoyl;
  6) —D—E, wherein D is selected from the group consisting of: $C_1$–$C_3$ straight alkyl, $C_3$ branched alkyl, $C_2$–$C_3$ straight alkenyl, $C_3$ branched alkenyl, $C_1$–$C_3$ straight alkoyl, aryl and aroyl; and E is selected from the group consisting of: —$(PO_3)_n$NMP, where n is 0–2 and NMP is ribonucleotide monophosphate connected via the 5'-phosphate, 3'-phosphate or the aromatic ring of the base; —[P(=O)(OCH$_3$)(O)]$_m$—Q, where m is 0–3 and Q is a ribonucleoside connected via the ribose or the aromatic ring of the base; —[P(=O)(OH)(CH$_2$)]$_m$—Q, where m is 0–3 and Q is a ribonucleoside connected via the ribose or the aromatic ring of the base; and an aryl group containing 0–3 substituents chosen independently from the group consisting of: Cl, Br, epoxy, acetoxy, —OG, —C(=O)G, and —$CO_2$G, where G is independently selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, $C_4$–$C_6$ branched alkoyl, wherein E may be attached to any point to D, and if D is alkyl or alkenyl, D may be connected at either or both ends by an amide linkage; and
  7) —E, wherein E is selected from the group consisting of —$(PO_3)_n$NMP, where n is 0–2 and NMP is a ribonucleotide monophosphate connected via the 5'-phosphate, 3'-phosphate or the aromatic ring of the base; —[P(=O)(OCH$_3$)(O)]$_m$—Q, where m is 0–3 and Q is a ribonucleoside connected via the ribose or the aromatic ring of the base; —[P(=O)(OH)(CH$_2$)]$_m$—Q, where m is 0–3 and Q is a ribonucleoside connected via the ribose or the aromatic ring of the base; and an aryl group containing 0–3 substituents chose independently from the group consisting of: Cl, Br, epoxy, acetoxy, —OG, —C(=O)G, and —CO₂G, where G is independently selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, $C_4$–$C_6$ branched alkoyl; and if E is aryl, E may be connected by an amide linkage;

e) if $R_1$ and at least one $R_2$ group are present, $R_1$ may be connected by a single or double bond to an $R_2$ group to form a cycle of 5 to 7 members;

f) if two $R_2$ groups are present, they may be connected by a single or a double bond to form a cycle of 4 to 7 members; and g) if $R_1$ is present and $Z_1$ or $Z_2$ is selected from the group consisting of —NHR₂, —CH₂R₂ and —NR₂OH, then $R_1$ may be connected by a single or double bond to the carbon or nitrogen of either $Z_1$ or $Z_2$ to form a cycle of 4 to 7 members.

Currently preferred compounds include cyclocreatine, creatine phosphate and those included in Tables 1 and 2 hereinabove.

The modes of administration for these compounds includes but is not limited to, oral, transdermal, or parenteral (eg., subcutaneous, intramuscular, intravenous, bolus or continuous infusion). The actual amount of drug needed will depend on factors such as the size, age and severity of disease in afflicted individual. Creatine has been given to athletes in the range of 2–8 gms/day to improve muscle function. Creatine phosphate was administered to patients with congestive heart failure also in the range of several gm/day and was very well tolerated. In experimental animal models of cancer or viral infections, were creatine compounds were shown to be active, amounts of 1 gm/kg/day were needed intraveniously or intraperitoneially. For this invention the creatine compound will be administered at dosages and for periods of time effective to reduce, ameliorate or eliminate the symptoms of the disease. Dose regimens may be adjusted for purposes of improving the therapeutic or prophylactic response of the compound. For example, several divided doses may be administered daily, one dose, or cyclic administration of the compounds to achieve the required therapeutic result.

The creatine compounds can be formulated according to the selected route of administration. The addition of gelatin, flavoring agents, or coating material can be used for oral applications. For solutions or emulsions in general, carriers may include aqueous or alcoholic/aqueous solutions, emulsions or suspensions, including saline and buffered media. Parenteral vehicles can include sodium chloride, potassium chloride among others. In addition intravenous vehicles can include fluid and nutrient replenishers, electrolyte replenishers among others.

Preservatives and other additives can also be present. For example, antimicrobial, antioxidant, chelating agents, and inert gases can be added (see, generally, Remington's Pharmaceutical Sciences, 16th Edition, Mack, 1980).

Equivalents

Those skilled in the art will recognize, or be able to ascertain using no more than routine experimentation many equivalents to the specific embodiments of the invention described herein. Such equivalents are intended to be encompassed by the following claims.

What is claimed is:

1. A method for regulating an imbalance of body weight in a subject, comprising administering to a subject a therapeutically effective amount of a creatine compound or a pharmaceutically acceptable salt, such that an imbalance of body weight in said subject is regulated.

2. The method of claim 1, wherein said imbalance of body weight is obesity.

3. The method of claim 1, wherein said imbalance of body weight is associated with a disorder.

4. The method of claim 3, wherein said disorder is hyperlipidemia.

5. The method of claim 3, wherein said disorder is cardiovascular disease.

6. The method of claim 3, wherein said disorder is diabetes.

7. The method of claim 3, wherein said disorder is osteoporosis.

8. The method of claim 3, wherein said disorder is osteoarthritis.

9. The method of claim 3, wherein said disorder is severe weight loss.

10. The method of claim 1, wherein said subject is a human.

11. The method of claim 1, wherein said creatine compound has the general formula:

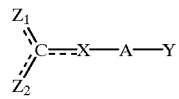

and pharmaceutically acceptable salts thereof, wherein:

a) Y is selected from the group consisting of: —CO₂H—NHOH, —NO₂, —SO₃H, —C(=O)NHSO₂J and —P(=O)(OH)(OJ), wherein J is selected from a group consisting of: hydrogen, $C_1$–$C_6$ straight chain alkyl, $C_3$–$C_6$ branched alkyl, $C_2$–$C_6$ alkenyl, $C_3$–$C_6$ branched alkenyl, and aryl;

b) A is selected from the group consisting of: C, CH, $C_1$–$C_5$ alkyl, $C_2$–$C_5$ alkenyl, $C_2$–$C_5$ alkynyl, and $C_1$–$C_5$ alkoyl chain, each having 0–2 substituents which are selected independently from the group consisting of:

1) K, where K is selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of bromo, chloro, epoxy and acetoxy;

2) an aryl group selected from the group consisting of: a 1–2 ring carbocycle and a 1–2 ring heterocycle, wherein the aryl group contains 0–2 substituents independently selected from the group consisting of: —CH₂L and —COCH₂L where L is independently selected from the group consisting of: bromo, chloro, epoxy and acetoxy; and 3) —NH—M, wherein M is selected from the group consisting of: hydrogen, $C_1$–$C_4$ alkyl, $C_2$–$C_4$ alkenyl, $C_1$–$C_4$ alkoyl, $C_3$–$C_4$ branched alkyl, $C_3$–$C_4$ branched alkenyl, and C4 branched alkoyl;

c) X is selected from the group consisting of NR₁, CHR₁, CR₁, O and S, wherein $R_1$ is selected from the group consisting of:

1) hydrogen;

2) K where K is selected from the group consisting of: $C_1$–$C_6$ straight alkyl, $C_2$–$C_6$ straight alkenyl, $C_1$–$C_6$ straight alkoyl, $C_3$–$C_6$ branched alkyl, $C_3$–$C_6$ branched alkenyl, and $C_4$–$C_6$ branched alkoyl, K having 0–2 substituents independently selected from the group consisting of: bromo, chloro, epoxy and acetoxy;
3) an aryl group selected from the group consisting of a 1–2 ring carbocycle and a 1–2 ring heterocycle, wherein the aryl group consisting of: —CH$_2$L and —COCH$_2$L where L is independently selected from the group consisting of: bromo, chloro, epoxy and acetoxy;
4) a C$_5$–C$_9$ α-amino-ω-adenosylcarboxylic acid attached via the ω-methyl carbon;
5) 2 C$_5$–C$_9$-α-amino-ω-aza-ω-methyl-ω-adenosylcarboxylic acid attached via the ω-methyl carbon;
6) a C$_5$–C$_9$ α-amino-ω-thia-ω-methyl-ω-adenosylcarboxylic acid attached via the ω-methyl carbon;

d) Z$_1$ and Z$_2$ are chosen independently from the group consisting, of; =O, —NHR$_2$, —CH$_2$R$_2$, —NR$_2$OH; wherein Z$_1$ and Z$_2$ may not both be =O and wherein R$_2$ is selected from the group consisting of:
1) hydrogen;
2) K, where K is selected from the group consisting of: C$_1$–C$_6$ straight alkyl; C$_2$–C$_6$ straight alkenyl, C$_1$–C$_6$ straight alkoyl, C$_3$–C$_6$ branched alkyl, C$_3$–C$_6$ branched alkenyl, and C$_4$–C$_6$ branched alkoyl, K having 0–2 substituents independently selected from the group consisting of: bromo, chloro, epoxy and acetoxy;
3) an aryl group selected from the group consisting of a 1–2 ring carbocycle and a 1–2 ring heterocycle, wherein the aryl group contains 0–2 substituents independently selected from the group consisting of: —CH$_2$L and —COCH$_2$L where L is independently selected from the group consisting of: bromo, chloro, epoxy and acetoxy;
4) 2 C$_4$–C$_8$ α-amino-carboxylic acid attached via the ω-carbon;
5) B, wherein B is selected from the group consisting of: —CO$_2$H—NHOH, —SO$_3$H, —NO$_2$, OP(=O)(OH)(OJ) and —P(=O)(OH)(OJ), wherein J is selected from the group consisting of: hydrogen, C$_1$–C$_6$ straight alkyl, C$_3$–C$_6$ branched alkyl, C$_2$–C$_6$ alkenyl, C$_3$–C$_6$ branched alkenyl, and aryl, wherein B is optionally connected to the nitrogen via linker selected from the group consisting of: C$_1$–C$_2$ alkyl, C$_2$ alkenyl, and C$_1$–C$_2$ alkoyl;
6) —D—E, wherein D is selected from the group consisting of: C$_1$–C$_3$ straight alkyl, C$_3$ branched alkyl, C$_2$–C$_3$ straight alkenyl, C$_3$ branched alkenyl, C$_1$–C$_3$ straight alkoyl, aryl and aroyl; and E is selected from the group consisting of: —(PO$_3$)$_n$NMP, where n is 0–2 and NMP is ribonucleotide monophosphate connected via the 5'-phosphate or the aromatic ring of the base; —[P(=O)(OCH$_3$)(O)]$_m$—Q, where m is 0–3 and Q is a ribonucleoside connected via the ribose or the aromatic ring of the base; and an aryl group containing 0–3 substituents chosen independently from the group consisting of: Cl, Br, epoxy, acetoxy, —OG, —C(=O)G, and —CO$_2$G, where G is independently selected from the group consisting of: C$_1$–C$_6$ straight alkyl, C$_2$–C$_6$ straight alkenyl, C$_1$–C$_6$ straight alkoyl, C$_3$–C$_6$ branched alkyl, C$_3$–C$_6$ branched alkenyl, C$_4$–C$_6$ branched alkoyl, wherein E may be attached to any point to D, and if D is alkyl or alkenyl, D may be connected at either or both ends by an amide linkage; and
7) —E, wherein E is selected from the group consisting of —(PO$_3$)$_n$NMP, where n is 0–2 and NMP is a ribonucleotide monophosphate connected via the 5'-phosphate, 3'-phosphate or the aromatic ring of the base; —[P(=O)(OCH$_3$)(O)]$_m$—Q where m is 0–3 and Q is a ribonucleoside connected via the ribose or the aromatic ring of the base; and an aryl group consisting of: Cl, Br, epoxy, acetoxy, —OG, —C(=O)G, and —CO$_2$G, where G is independently selected from the group consisting of: C$_1$–C$_6$ straight alkyl, C$_2$–C$_6$ straight alkenyl, C$_1$–C$_6$ straight alkoyl, C$_3$–C$_6$ branched alkyl, C$_3$–C$_6$ branched alkenyl, C$_4$–C$_6$ branched alkoyl; and if E is aryl, E may be connected by an amide linkage;

e) if R$_1$ and at least one R$_2$ group are present, R$_1$ may be connected by a single or double bond to an R$_2$ group to form a cycle of 5 to 7 members;

f) if two R$_2$ groups are present, they may be connected by a single or a double bond to form a cycle of 4 to 7 members; and g) if R$_1$ is present and Z$_1$ or Z$_2$ is selected from the group consisting of —NHR$_2$, —CH$_2$ R$_2$—CH$_2$ $_{R2}$ and —NR$_2$OH, then R$_1$ may be connected by a single or double bond to the carbon or nitrogen of either Z$_1$ or Z$_2$ to form a cycle of 4 to 7 members.

12. The method of claim 11, wherein said creatine compound is creatine or cyclocreatine.

13. The method of claim 11, wherein said creatine compound is a creatine phosphate analogue.

14. The method of claim 13, wherein said creatine phosphate analogue is creatine phosphate.

15. A method of, treating or preventing a body disorder related to weight gain or loss, comprising:
administering to a subject afflicted with or susceptible to said disorder, an amount of a creatine compound, or a pharmaceutically acceptable salt thereof effective to treat, reduce or prevent said disorder, wherein said disorder is obesity.

16. A method of, treating or preventing a body disorder related to weight gain or loss, comprising:
administering to a subject afflicted with or susceptible to said disorder, an amount of a creatine compound, or a pharmaceutically acceptable salt thereof effective to treat, reduce or prevent said disorder, wherein said disorder is cachexia.

17. A method of, treating or preventing a body disorder related to weight gain or loss, comprising:
administering to a subject afflicted with or susceptible to said disorder, an amount of a creatine compound, or a pharmaceutically acceptable salt thereof effective to treat, reduce or prevent said disorder, wherein said disorder is hypertension.

18. A method of, treating or preventing a body disorder related to weight gain or loss, comprising:
administering to a subject afflicted with or susceptible to said disorder, an amount of a creatine compound, or a pharmaceutically acceptable salt thereof effective to treat, reduce or prevent said disorder, wherein said disorder is osteoporosis.

19. A method of, treating or preventing a body disorder related to weight gain or loss, comprising:

administering to a subject afflicted with or susceptible to said disorder, an amount of a creatine compound, or a pharmaceutically acceptable salt thereof effective to treat, reduce or prevent said disorder, wherein said disorder is osteoarthritis.

20. The method of any one of claims 15, 16, and 17–19, wherein said subject is a human.

* * * * *